United States Patent [19]
Atwell et al.

[11] Patent Number: 5,396,071
[45] Date of Patent: Mar. 7, 1995

[54] MODULARIZED ASSEMBLY FOR BULK MATERIAL ANALYZER

[75] Inventors: Thomas L. Atwell, La Jolla; Chris A. Isaacson, Poway; Andrew H. Smith, Escondido; James P. Stronski; Richard A. Ackermann, both of San Diego, all of Calif.

[73] Assignee: Gamma-Metrics, San Diego, Calif.

[21] Appl. No.: 89,273

[22] Filed: Jul. 9, 1993

[51] Int. Cl.⁶ .................. G01N 23/02; G01N 23/12; B65G 53/00
[52] U.S. Cl. .................. 250/358.1; 250/359.1; 250/390.04; 376/157; 198/811
[58] Field of Search .................. 250/359.1, 358.1, 388, 250/394, 390.04; 376/157, 159; 198/811

[56] References Cited
U.S. PATENT DOCUMENTS

| | | | |
|---|---|---|---|
| 3,053,388 | 9/1962 | Tittle | 250/339.1 |
| 3,583,551 | 6/1971 | Barnish | 198/811 |
| 3,748,473 | 7/1973 | Chen | 250/394 |
| 4,428,902 | 1/1984 | Murray | 376/157 |
| 4,550,823 | 11/1985 | Gladish | 198/811 |
| 4,582,992 | 4/1986 | Atwell et al. | 250/359.1 |
| 5,162,096 | 11/1992 | Gozani | 376/159 |

*Primary Examiner*—Paul M. Dzierzynski
*Assistant Examiner*—Drew A. Dunn
*Attorney, Agent, or Firm*—Edward W. Callan

[57] ABSTRACT

A bulk material analyzer of the type in which the bulk material is transported through the material analyzer assembly on a conveyor belt between at least one radiation source and at least one radiation detector, includes a plurality of lower and upper modules that contain radiation shielding material and are so shaped as to define a passageway for the conveyor belt between the upper modules and the lower modules when the upper modules are placed on the lower modules. A primary centrally located lower module also includes the radiation sources and a primary centrally located upper module also includes the radiation detectors. Some of the outwardly located modules contain less radiation shielding material. The radiation shielding material includes a plurality of personally portable blocks. The conveyor belt is supported by compressed air passed through central upper wails in the outwardly located lower modules. The lower modules contain alignment members on upward facing surfaces thereof and the upper modules contain alignment members on downward facing surfaces thereof that are complementary to the alignment members on the upward facing surfaces in order to enable the upper modules to be accurately placed on the lower modules. The lower modules each include a central upper wall bounded by outwardly inclined inner side walls to define a trough for accommodating passage through the passageway of a conveyor belt having a contour corresponding to the trough. The container includes apertures disposed beneath at least part of the passageway, and includes conduits leading to the apertures from a port adapted to be connected to a source of compressed air so that the conveyor belt can be at least partially supported by compressed air while passing through the passageway.

11 Claims, 2 Drawing Sheets

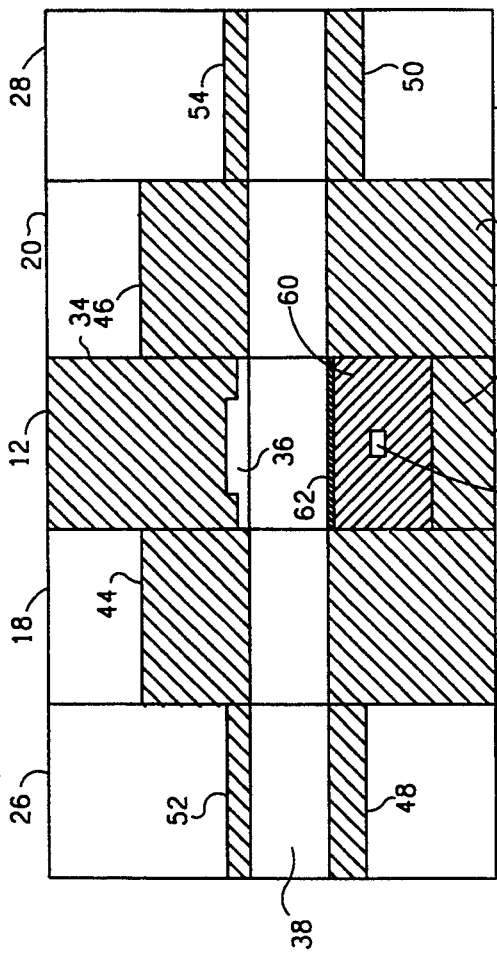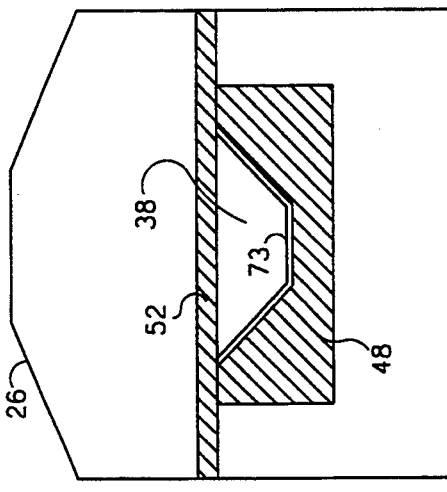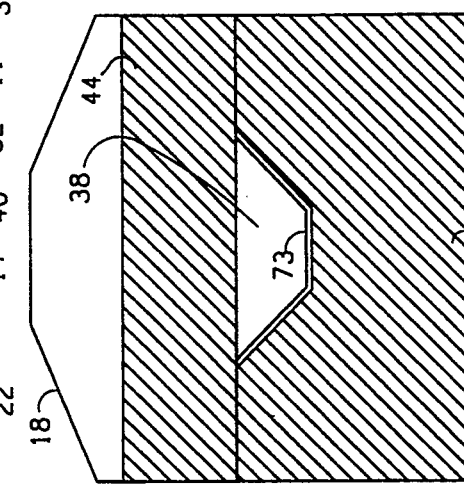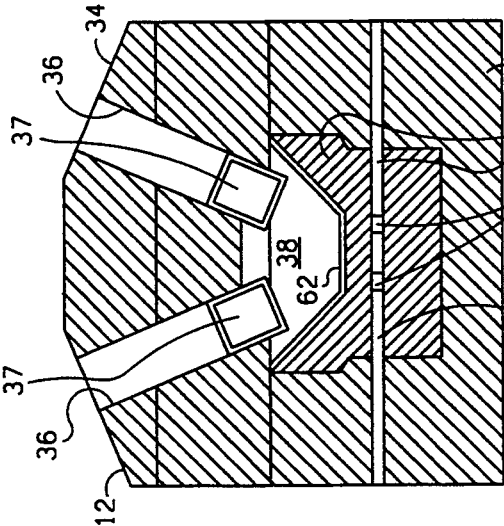

MODULARIZED ASSEMBLY FOR BULK MATERIAL ANALYZER

GROUND OF THE INVENTION

The present invention generally pertains to bulk material analyzers and is particularly directed to an improved assembly for bulk material analyzers of the type in which the bulk material is transported through the material analyzer on a conveyor belt between at least one radiation source and at least one radiation detector.

Bulk material analyzers are used to measure the elemental content of bulk materials. In one type of bulk material analyzer, the radiation source includes one or more neutron sources and the radiation detector includes one or more gamma-ray detectors that produce signals which are processed to provide a measurement of the elemental content of the bulk material. When the bulk material is bombarded by neutrons, secondary emissions of gamma-rays are produced from the bulk material. Different characteristic gamma-ray energy spectra are produced from different elements in the bulk material. By processing detected signals that are indicative of the gamma-ray spectrum a measurement is provided of the elemental content of the bulk material. This measurement process is known in the art as prompt gamma-ray neutron activation analysis (PGNAA). In addition to containing the radiation source and the radiation detector, the bulk material analyzer assembly necessarily includes a large quantity of radiation shielding material in order to protect persons using the bulk material analyzer from harmful dosages of radiation. The required quantity of radiation shielding material is such that the bulk material analyzer assembly is so large that the assembly is not easily handled for transportation from one site to another.

SUMMARY OF THE INVENTION

The present invention provides an improved assembly for a bulk material analyzer of the type in which bulk material is transported through the assembly on a conveyor belt between at least one radiation source and at least on radiation detector, said assembly comprising container means defining at least one radiation source cavity, at least one radiation detector cavity and a passageway disposed for enabling passage of a conveyor belt between the at least one radiation source cavity and the at least one radiation detector cavity; and radiation shielding material disposed within the container means; wherein the container means include a lower primary module containing a first portion of the radiation shielding material and defining either said at least one radiation source cavity or said at least one radiation detector cavity; an upper primary module containing a second portion of the radiation shielding material and defining whichever of either said at least one radiation source cavity or said at least one radiation detector cavity is not defined by the lower primary module; wherein the lower primary module and the upper primary module are so shaped that a first portion of the passageway is define by placement of the upper primary module, on top of the lower primary module; a pair of lower secondary modules for placement on opposite sides of the lower primary module along the path of the passageway and respectively containing third and fourth portions of the radiation shielding material; and a pair of upper secondary modules for placement on opposite sides of the upper primary module along the path of the passageway and respectively containing fifth and sixth portions of the radiation shielding material; wherein the lower secondary modules and the upper secondary modules are so shaped that additional portions of the passageway are defined by placement of the upper secondary modules on top of the lower secondary modules.

By assembling the bulk material analyzer from such individual modules that easily can be handled separately, the bulk material analyzer assembly is more easily handled for transportation from one site to another, with the assembly easily being completed at a site where the bulk material analyzer is to be used.

Also, the bulk material analyzer of the present invention may readily be assembled about an in-place conveyor belt without having to sever the belt.

In another aspect, the present invention provides an assembly for a bulk material analyzer of the type in which the bulk material is transported through the assembly on a conveyor belt between at least one radiation source and at least one radiation detector, said assembly comprising a container assembly defining at least one radiation source cavity, at least one radiation detector cavity, and a passageway disposed for enabling passage of a conveyor belt between the at least one radiation source cavity and the at least one radiation detector cavity, wherein the container further defines apertures disposed beneath only portions of the passageway, that precede and follow a portion of the passageway directly between the at least one radiation source and the at least one radiation detector, and includes conduits for connecting said apertures to a source of compressed air so that the conveyor belt can be at least partially supported by compressed air while passing through the passageway.

Additional features of the present invention are described in relation to the detailed description of the preferred embodiment.

BRIEF DESCRIPTION OF THE DRAWING

FIG. 3 is a sectional elevation view of the modules included in the assembly of FIG. 1 taken along lines 3—3.

FIG. 4 is a sectional elevation view of the primary modules included in the assembly of FIG. 1 taken along lines 4—4.

FIG. 5 is a sectional elevation view of a combined set the secondary modules included in the assembly of FIG. 1 taken along lines 5—5.

FIG. 6 is a sectional elevation view of a combined set of the tertiary modules included in the assembly of FIG. 1 taken along lines 6—6.

DETAILED DESCRIPTION

Figure 1:
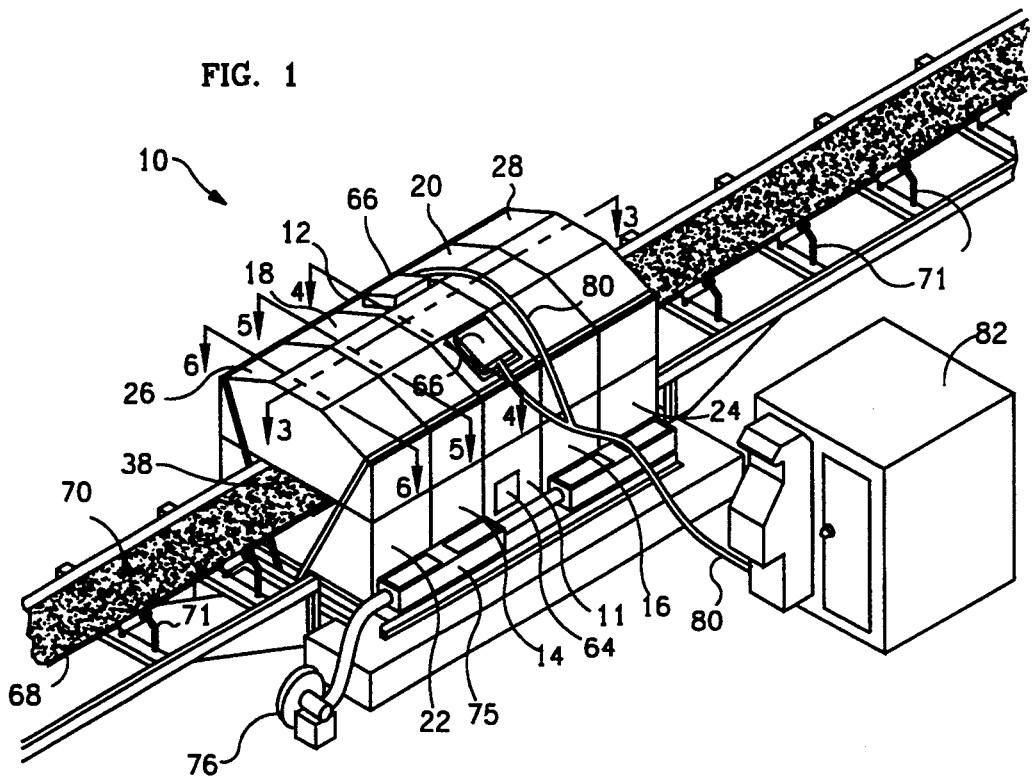
FIG. 1 is a perspective view illustrating a preferred embodiment the bulk material analyzer assembly of the present invention with a conveyor belt transporting bulk material through the material analyzer assembly.
Figure 2:
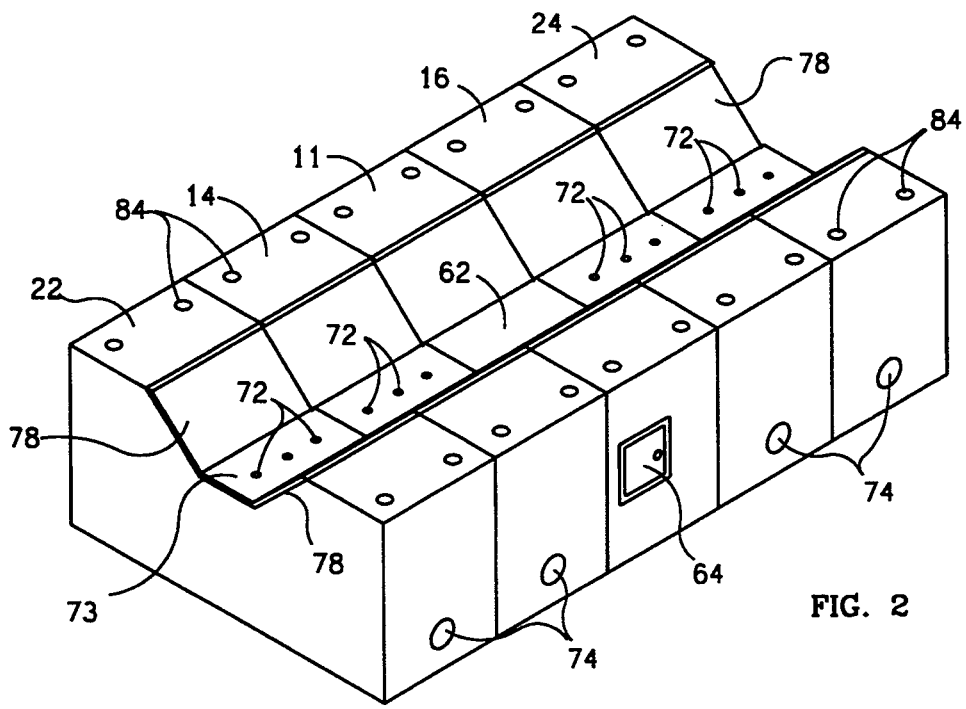
FIG. 2 is a perspective view of the assembled lower modules included in the assembly of FIG. 1.

Referring to FIGS. 1 and 2, a preferred embodiment of the bulk material analyzer assembly 10 of the present invention includes a lower primary module 11, an upper primary module 12, a first lower secondary module 14, a second lower secondary module 16, a first upper secondary module 18, a second upper secondary module 20, a first lower tertiary module 22, a second lower tertiary module 24, a first upper tertiary module 26 and a second upper tertiary module 28.

The lower primary module 11 contains a first portion of radiation shielding material 30 and defines a pair of radiation source cavities 32 for receiving neutron sources 33, as shown in FIGS. 3 and 4. The upper primary module 12 contains a second portion of radiation shielding material 34 and defines a pair of radiation detector cavities 36 for receiving gamma-ray detectors 37, as also shown in FIGS. 3 and 4. The lower primary module 11 and the upper primary module 12 are so shaped that the upper primary module 12 can be placed on top of the lower primary module 11 to define a first portion of a passageway 38.

The first and second lower secondary modules 14, 16 are placed on opposite sides of the lower primary module 11 along the path of the passageway 38. The first lower secondary module 14 contains a third portion of radiation shielding material 40, as shown in FIGS. 3 and 5. The second lower secondary module 16 contains a fourth portion of radiation shielding material 42, as shown in FIG. 3.

The first and second upper secondary modules 18, 20 are placed on opposite sides of the upper primary module 12 along the path of the passageway 38. The first upper secondary module 18 contains a fifth portion of radiation shielding material 44, as shown in FIGS. 3 and 5. The second upper secondary module 20 contains a sixth portion of radiation shielding material 46, as shown in FIG. 3. Each of the fifth portion of radiation shielding material 44 and the sixth portion of radiation shielding material 46 is less than the second portion of radiation shielding material 34 in the upper primary module 12.

The lower secondary modules 14, 16 and the upper secondary modules 18, 20 are so shaped that the upper secondary modules 18, 20 can be placed on top of the lower secondary modules 14, 16 to define additional portions of the passageway 38 that are continuous with the first portion of the passageway 38 defined by the upper and lower primary modules 11, 12.

The first and second lower tertiary modules 22, 24 are placed on opposite sides of the assemblage of the lower primary module 11 and the lower secondary modules 14, 16 along the path of the passageway 38. The first lower tertiary module 22 contains a seventh portion of radiation shielding material 48, as shown in FIGS. 3 and 6. The second lower tertiary module 24 contains a eighth portion of radiation shielding material 50, as shown in FIG. 3. Each of the seventh portion of radiation shielding material 48 and the eighth portion of radiation shielding material 50 is less than each of the third portion of radiation shielding material 40 and the fourth portion of radiation shielding material 42 in the lower secondary modules 14, 16.

The first and second upper tertiary modules 26, 28 are placed on opposite sides of the assemblage of the upper primary module 12 and the upper secondary modules 18, 20 along the path of the passageway 38. The first upper tertiary module 26 contains a ninth portion of radiation shielding material 52, as shown in FIGS. 3 and 6. The second upper tertiary module 28 contains a tenth portion of radiation shielding material 54. Each of the ninth portion of radiation shielding material 52 and the tenth portion of radiation shielding material 54 is less than each of the fifth portion of radiation shielding material 44 and the sixth portion of radiation shielding material 46 in the upper secondary modules 18, 20.

The lower tertiary modules 22, 24 and the upper secondary modules 26, 28 are so shaped that the upper tertiary modules 26, 28 can be placed on top of the lower tertiary modules 22, 24 to define further portions of the passageway 38 that are continuous with the additional portions of the passageway 38 defined by the upper and lower secondary modules 14, 16, 18, 20.

The passageway 38 is disposed for enabling passage of a conveyor belt between the radiation source cavities 32 and the radiation detector cavities 36.

In each of the ten modules, 11, 12, 14, 16, 18, 20, 22, 24, 26, 28, the radiation shielding material 30, 34, 40, 42, 44, 46, 48, 50, 52, 54 is cast within the modules upon manufacture of the modules. In alternative embodiments, the radiation shielding material may include sheets or blocks that are installed in one or more of the modules after having been cast outside the modules. Such blocks and/or sheets of radiation material may be installed either separately or in combination with radiation shielding material that was cast within the modules. Preferably, the blocks are of such dimensions and weight that they are personally portable for easy installation.

The lower primary module 11 also includes neutron moderating material 60 disposed between the radiation source cavities 32 and the radiation shielding material 30, and a window 62 of neutron transmissive material at the surface of the lower primary module 11 facing the passageway 38. The subject matter of this paragraph is claimed in a United States patent application being filed by Thomas L. Atwell, et at., entitled "Enhancement of Measurement Accuracy in Bulk Material Analyzer", and bearing Attorney Docket No. 33-54.

The radiation source cavities 32 lead to the sides of the lower primary module 11 and are accessible by opening hatches 64 on opposite sides of the lower primary module 11. The hatches 64 are closed after the neutron sources 33 have been inserted into the radiation source cavities 32.

The upper primary module 12 includes a pair of hatches 66, which are opened to access the radiation detector cavities 36 for installing and removing the gamma-ray detectors 37.

FIG. 1 also illustrates a conveyor belt 68 for transporting bulk material 70 through the passageway 38 in the bulk material analyzer assembly 10. The conveyor belt 68 is supported by a plurality of metal support assemblies 71.

Each of the secondary and tertiary lower modules 14, 16, 22, 24 defines apertures 72 in central upper walls 73 of said modules disposed beneath positions occupied by the conveyor belt 68 when the conveyor belt 68 is disposed for passage through the passageway 38, and includes conduits (not shown) leading to the apertures 72 from a port 74, which is adapted to be connected by a coupling assembly 75 to a source of compressed air 76, so that the conveyor belt 68 can be at least partially supported by compressed air while passing over the primary lower module 11. This feature minimizes abrasion of the graphite window 62 by contact with conveyor belt 68 while the conveyor belt 68 is moving. The use of compressed air to support the conveyor belt 68 avoids having to place within the passageway 38 the metal conveyor supports 71 that support the conveyor belt 68 outside of the passageway 38, and which would affect measurements made by the bulk material analyzer if such support assemblies 71 were placed within the passageway 38, since such metal support assemblies 71 would provide an additional source of secondary gamma-ray emission.

The central upper walls 73 of the lower modules 11, 14, 16, 22, 24 are bounded by outwardly inclined inner side walls 78 to define a trough having a contour corresponding to the contour of the conveyor belt 68 for accommodating passage of the conveyor belt 68 through the passageway 38.

The gamma-ray detectors 37 are connected by electrical cables 80 to a data processor within a separate housing 82. The data processor processes signals produced by the gamma-ray detectors to measure the elemental content of the bulk material being transported by the conveyor 68 through the bulk material analyzer assembly 10.

In order to assure that the upper modules 12, 18, 20, 26, 28 are accurately placed on the respective lower modules 11, 14, 16, 26, 28, the lower modules contain alignment members 84 on upward facing surfaces thereof and the upper modules contain alignment members (not shown) on downward facing surfaces thereof that are complementary to the alignment members 84 on the upward facing surfaces of the lower modules. For example, the alignment members 84 may be concave hemispheres and the complementary alignment members on the downward facing surfaces of the upper modules may be convex hemispheres.

We claim:

1. An assembly for a bulk material analyzer of the type in which bulk material is transported through the assembly on a conveyor belt between at least one radiation source and at least one radiation detector, said assembly comprising container means defining at least one radiation source cavity, at least one radiation detector cavity and a passageway disposed for enabling passage of a conveyor belt between the at least one radiation source cavity and the at least one radiation detector cavity; and radiation shielding material disposed within the container means;

wherein the container means include a lower primary module containing a first portion of the radiation shielding material and defining either said at least one radiation source cavity or said at least one radiation detector cavity;

an upper primary module containing a second portion of the radiation shielding material and defining whichever of either said at least one radiation source cavity or said at least one radiation detector cavity is not defined by the lower primary module;

wherein the lower primary module and the upper primary module are so shaped that a first portion of the passageway is defined by placement of the upper primary module on top of the lower primary module;

a pair of lower secondary modules for placement on opposite sides of the lower primary module along the path of the passageway and respectively containing third and fourth portions of the radiation shielding material; and a pair of upper secondary modules for placement on opposite sides of the upper primary module along the path of the passageway and respectively containing fifth and sixth portions of the radiation shielding material;

wherein the lower secondary modules and the upper secondary modules are so shaped that additional portions of the passageway are defined by placement of the upper secondary modules on top of the lower secondary modules.

2. An assembly according to claim 1, further comprising a pair of lower tertiary modules for placement on opposite sides of the assemblage of the lower primary module and the lower secondary modules along the path of the passageway and respectively containing seventh and eighth portions of the radiation shielding material; and a pair of upper tertiary modules for placement on opposite sides of the assemblage of the upper primary module and the upper secondary modules along the path of the passageway and respectively containing ninth and tenth portions of the radiation shielding material;

wherein the lower tertiary modules and the upper tertiary modules are so shaped that further portions of the passageway are defined by placement of the upper tertiary modules on top of the lower tertiary modules.

3. An assembly according to claim 2, wherein each of the secondary and tertiary lower modules, but not any portion of the primary lower module directly between the at least one radiation source and the at least one radiation detector, defines apertures in the portions of said modules disposed beneath positions occupied by the conveyor belt when the conveyor belt is disposed for passage through the passageway, and includes conduits for connecting said apertures to a source of compressed air so that the conveyor belt can be at least partially supported by compressed air while passing over the primary lower module.

4. An assembly according to claim 2, wherein each of said filth and sixth portions of radiation shielding material is less than said second portion of the radiation shielding material; each of said seventh and eighth portions of radiation shielding material is less than each of said third and fourth portions of the radiation shielding material; and each of said ninth and tenth portions of radiation shielding material is less than each of said filth and sixth portions of the radiation shielding material.

5. An assembly according to claim 1, wherein each of said fifth and sixth portions of radiation shielding material is less than said second portion of the radiation shielding material.

6. An assembly according to claim 1, wherein each of the secondary lower modules, but not any portion of the primary lower module between the at least radiation source and the at least one radiation detector, define apertures in the portions of said modules disposed beneath positions occupied by the conveyor belt when the conveyor belt is disposed for passage through the passageway, and includes conduits for connecting said apertures to a source of compressed air so that the conveyor belt can be at least partially supported by compressed air while passing over the secondary lower modules.

7. An assembly according to claim 1, wherein the radiation shielding material in at least one of the modules comprises a plurality of blocks of radiation shielding material.

8. An assembly according to claim 1, wherein the radiation shielding material in at least one of the modules comprises a plurality of personally portable blocks of radiation shielding material.

9. An assembly according to claim 1, wherein the lower modules contain alignment members on upward facing surfaces thereof and the upper modules contain alignment members on downward facing surfaces thereof that are complementary to the alignment members on said upward facing surfaces in order to enable the upper modules to be accurately placed on the lower modules.

10. An assembly according to claim 1, wherein the lower modules each include a central upper wall bounded by outwardly inclined inner side walls to define a trough for accommodating passage through the passageway of a conveyor belt having a contour corresponding to said trough.

11. An assembly for a bulk material analyzer of the type in which bulk material is transported through the assembly on a conveyor belt between at least one radiation source and at least one radiation detector, said assembly comprising a container assembly defining at least one radiation source cavity, at least one radiation detector cavity, and a passageway disposed for enabling passage of a conveyor belt between the at least one radiation source cavity and the at least one radiation detector cavity, wherein the container includes apertures disposed beneath only portions of the passageway that precede and follow a portion of the passageway directly between the at least one radiation source and the at least one radiation detector, and includes conduits for connecting said apertures to a source of compressed air so that the conveyor belt can be at least partially supported by compressed air while passing through the passageway.

* * * * *